US00PP32168P3

(12) United States Plant Patent
Biancheri

(10) Patent No.: US PP32,168 P3
(45) Date of Patent: Sep. 8, 2020

(54) ***RANUNCULUS* PLANT NAMED 'ABOTSO'**

(50) Latin Name: *Ranunculus asiaticus*
Varietal Denomination: ABOTSO

(71) Applicant: Alberto Biancheri, Camporosso Mare (IT)

(72) Inventor: Alberto Biancheri, Camporosso Mare (IT)

(73) Assignee: Impresa Individuale Biancheri Alberto (IT)

( * ) Notice: Subject to any disclaimer, the term of this patent is extended or adjusted under 35 U.S.C. 154(b) by 0 days.

(21) Appl. No.: 16/501,687

(22) Filed: May 21, 2019

(65) Prior Publication Data

US 2019/0373791 P1 Dec. 5, 2019

(30) Foreign Application Priority Data

May 31, 2018 (QZ) ..... PBR 2018/1412

(51) Int. Cl.
*A01H 5/02* (2018.01)
*A01H 6/72* (2018.01)

(52) U.S. Cl.
USPC ..... Plt./263.1
CPC ..... *A01H 6/72* (2018.05)

(58) Field of Classification Search
USPC ..... Plt./263.1
CPC ..... A01H 6/72
See application file for complete search history.

*Primary Examiner* — Anne Marie Grunberg
(74) *Attorney, Agent, or Firm* — Cassandra Bright

(57) ABSTRACT

A new and distinct cultivar of *Ranunculus* plant named 'ABOTSO' is disclosed, characterized by light pink flowers and a large corolla. Plants produce a high quantity of quality, large size flowers throughout the harvest season. The new variety is a *Ranunculus*, normally produced as a cut flower and potentially useful as an ornamental plant.

3 Drawing Sheets

Latin name of the genus and species: *Ranunculus asiaticus*.

Variety denomination: 'ABOTSO'.

BACKGROUND OF THE INVENTION

The new *Ranunculus* cultivar is a product of a planned breeding program conducted by the inventor, Alberto Biancheri at a research nursery in Camporosso Mare, Italy. The cross resulting in this new variety was made during 2010.

The seed parent is the unpatented, proprietary variety referred to as *Ranunculus* 'ABROCHI'. The pollen parent is the unpatented, proprietary variety referred to as *Ranunculus* '131-07/A'. The new variety was discovered in 2015 by the inventor in a group of seedlings resulting from the 2010 crossing, in a research greenhouse in Camporosso Mare, Italy.

Asexual reproduction of the new cultivar was first performed by vegetative division of buds sprouting from the rhizome of the selected plant. Subsequent propagation has been performed by tissue culture. First propagation took place at a research greenhouse in Camporosso Mare, Italy in 2015 and has shown that the unique features of this cultivar are stable and reproduced true to type in multiple successive generations.

SUMMARY OF THE INVENTION

The cultivar 'ABOTSO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ABOTSO' These characteristics in combination distinguish 'ABOTSO' as a new and distinct *Ranunculus* cultivar:

1. Light pink flowers.
2. Consistently large corolla production throughout harvest season.
3. High productivity of consistently quality flowers.

PARENT COMPARISON

Plants of the new cultivar 'ABOTSO' are similar to plants of the seed parent, in most horticultural characteristics, however, plants of the new cultivar 'ABOTSO' differ in the following;

1. Flower color of the new variety is lighter pink than that of the seed parent.
2. Vegetative carriage of the new variety is higher than that of the seed parent.

Plants of the new cultivar 'ABOTSO' are similar to plants of the pollen parent, in most horticultural characteristics, however, plants of the new cultivar 'ABOTSO' differ in the following;

1. Flower color of the new variety is different than that of the pollen parent.
2. Flower size of the new variety is larger than that of the pollen parent.

COMMERCIAL COMPARISON

Plants of the new cultivar 'ABOTSO' are comparable to the unpatented commercial variety *Ranunculus* 'ABROCHI'. The two *Ranunculus* varieties are similar in most horticultural characteristics; however, the new variety 'ABOTSO' differs in the following:

1. Flower color of the new variety is lighter pink.
2. Vegetative carriage of the new variety is higher.

BRIEF DESCRIPTION OF THE PHOTOGRAPHS

Figure 1:
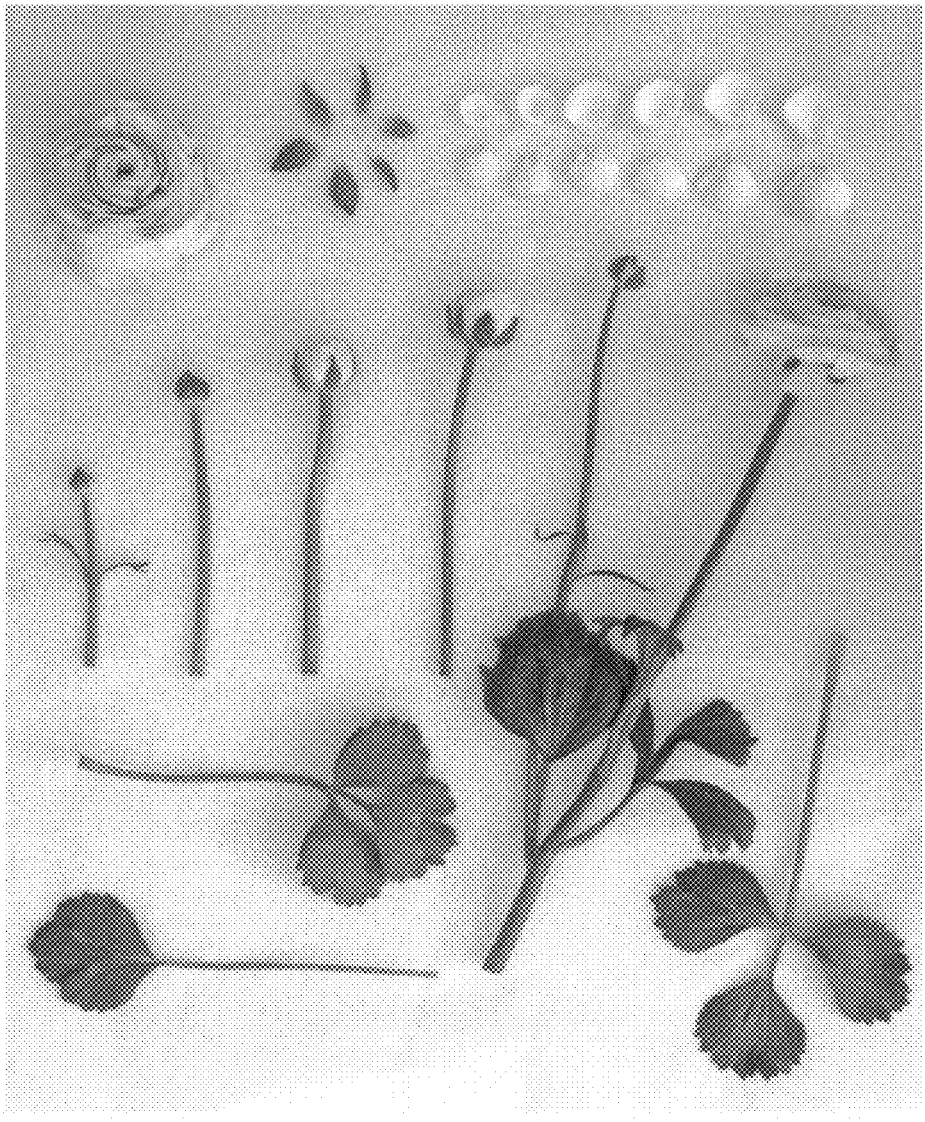

The accompanying photograph in FIG. 1 illustrates a close-up of plant parts.

Figure 2:
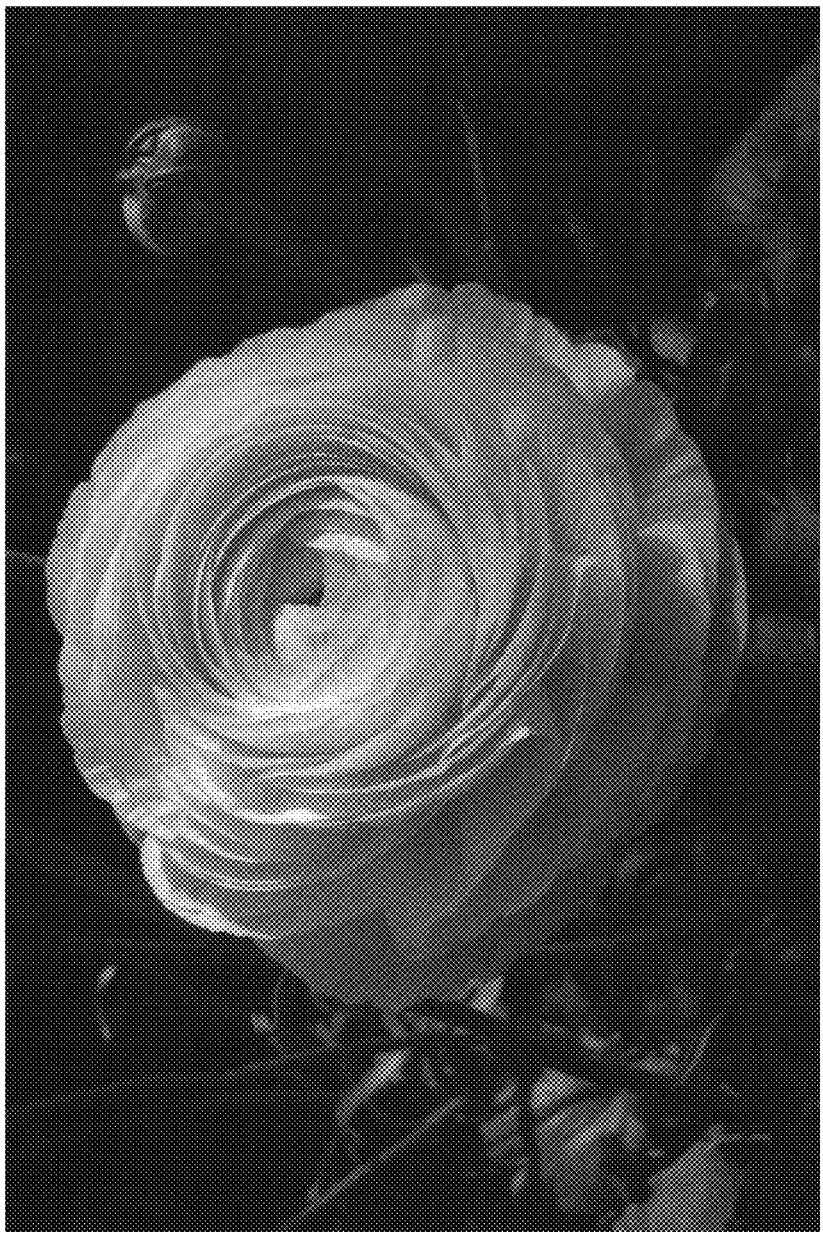

FIG. 2 illustrates a close-up view of a typical flower.

Figure 3:
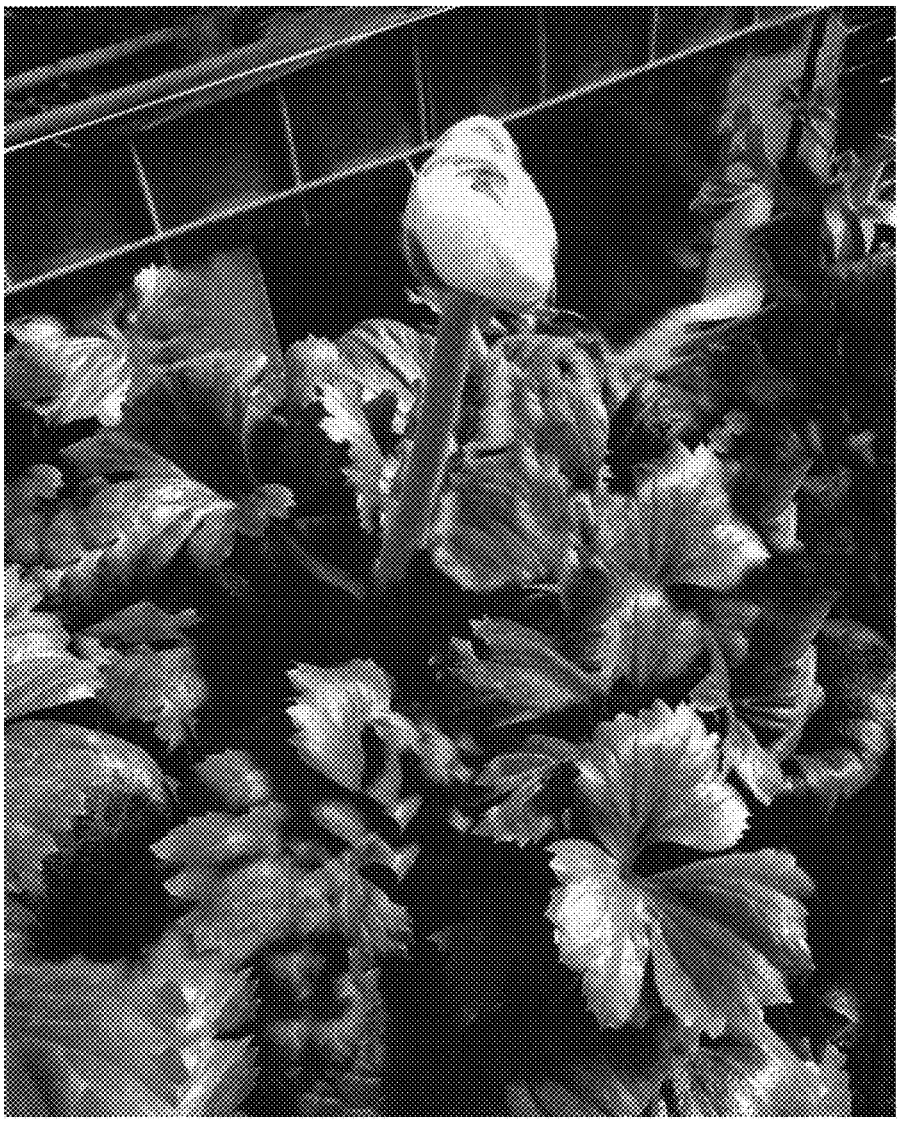

FIG. 3. illustrates in full color flowering plants of the new variety at approximately five months old, grown in a greenhouse.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ edition, except where general terms of ordinary dictionary significance are used. The following observations and measurements describe 5-month-old 'ABOTSO' plants grown in a greenhouse in Camporosso Mare, Italy. The plant described has been cultivated in the month of March. In order to protect the crop against pests, some chemical treatments are performed. Treatments with growth regulators can be performed to limit the plant sizes. In particular, no growth regulators have been applied on the plant described. The rhizome has been planted on raised benches in a peat and pumice substrate mixture. The growing temperature ranged from 12° C. to 24° C. during the day and from 0° C. to 6° C. during the night. General light conditions are bright, normal sunlight. Measurements and numerical values represent averages of typical plant types.

Botanical classification: *Ranunculus asiaticus* 'ABOTSO'.

Propagation:

*Time to rooting.*—15 days at approximately 10-12° C.

*Time to produce a rooted plantlet.*—20 days.

*Root description.*—Tuberous root.

Plant:

*Growth habit.*—Herbaceous perennial, robust plant, erect vegetation, compact.

*Height to top flower.*—Average range 50 to 55 cm.

*Leaf height.*—Average range 40 to 50 cm.

*Plant spread.*—Average range 50 to 55 cm.

*Growth rate.*—Medium.

*Branching characteristics.*—Main floral stems grow from a basal rosette with 1 or 2 lateral branches, each one of which has 1 or 2 flowers.

*Length of lateral branches.*—Average range 50 to 55 cm.

*Diameter of lateral branches.*—Average range 0.6 to 0.8 cm.

*Texture of lateral branches.*—Slightly tomentose.

*Internode length.*—Internodes are extremely close together, forming a basal rosette.

*Strength of lateral branches.*—Strong.

*Color of lateral branches.*—RHS Yellow Green 144A.

*Aspect/angle of branches.*—15° to 20°.

*Number of leaves per lateral branch.*—*Usually* 2.

Foliage: The plant has a marked heterophylly that means that in the same plant the leaves may have different size and arrangement (simple, ternate and biternate), in relation to the degree of development (young leaf and mature leaf) and their position on the plant (basal leaf—leaf at the base of the plant—and cauline leaf—leaf inserted at the nodes of the floral stems). In other words, there are significant variation in leaf shape on a same plant.

*Leaf at the base of the plant.*—Arrangement: Young Leaf: Simple. Mature Leaf: Ternate. Average Length: 25 to 30 cm. Average Width: 12 to 16 cm. Overall Shape of blade: Young Leaf: Obovate. Mature Leaf: Palmatipartite. Dissected leaves, describe lobes, quantity of dissection: Young leaves are generally slightly lobed; mature leaves are generally divided in 3 lobes, each one of which further divided. Apex: Rounded. Base: Acute. Attachment: Base of the plant. Margin: Dentate. Texture of top surface: Slightly tomentose. Texture of bottom surface: Slightly tomentose. Appearance of top surface: Matte. Appearance bottom surface: Matte. Leaf internode length: The internodes are extremely close together, forming a basal rosette. Color: Young foliage upper side: RHS Green 138A. Young foliage under side: RHS Green 138B. Mature foliage upper side: RHS Green 138A. Mature foliage under side: RHS Green 138B. Venation: Type: Dichotomous; plunging into the limb at the upper surface; raised on the limb at the lower surface. Venation color upper side: RHS Yellow-Green 144A. Venation color under side: RHS Yellow-Green 144A. Petiole: Appearance: Long, tubular. Length: Average range 12 to 15 cm. Diameter: Average range 0.3 to 0.6 cm. Pubescence: Slightly tomentose. Color: RHS Yellow-Green 144A.

*Leaf inserted at the nodes of the floral stems.*—Arrangement: Ternate. Average Length: 7 to 13 cm. Average Width: 5 to 10 cm. Overall Shape of blade: Palmatipartite. Dissected leaves, describe lobes, quantity of dissection: Generally simple or divided in 2 or 3 lobes. Apex: Acute. Base: Acute. Attachment: Floral stems. Margin: Dentate. Texture of top surface: Slightly tomentose. Texture of bottom surface: Slightly tomentose. Appearance of top surface: Matte. Appearance bottom surface: Glossy. Leaf internode length: Average 2 to 4 cm. Color: Foliage upper side: RHS Green 138A. Foliage under side: RHS Green 138B. Venation: Type: Dichotomous, plunging into the limb at the upper surface and raised on the limb at the lower surface. Venation color upper side: RHS Yellow-Green 144A. Venation color under side: RHS Yellow-Green 144A. Petiole: Appearance: Slightly flat. Length: Average 2 to 3 cm. Diameter: Average 0.1 to 0.3 cm. Pubescence: Slightly tomentose. Color: RHS Yellow-Green 144A.

Flower:

*Quantity per plant.*—8 to 10.

*Bloom period.*—Winter to Spring.

*Vase life* (*cut flower*).—20 to 25 days.

*Persistent or self-cleaning.*—Self-Cleaning.

*Bud.*—Closed bud: Shape: Flattened globular with a sharp point. Length: Average range 1.5 to 3.0 cm. Diameter: Average range 1.5 to 2.5 cm. Color: RHS Green 138A. Slightly open bud: Shape: Flattened globular with a sharp point. Length: Average range 2.5 to 3.0 cm. Diameter: Average range 2.5 to 3.0 cm. Color: RHS Yellow-Green 150D at base; Red 49D at margin.

*Flower.*—Diameter: Average range 8 to 10 cm. Height: Average range 3 to 4 cm.

*Corolla.*—Round, regular, in the form of a flat section.

*Petals.*—Arrangement: Imbricated, disposed on the receptacle in very tight verticils. The size of the petals is quite variable, according to the position in the corolla, decreasing from the exterior toward the center. Lobe Length: Average range 4.5 to 6.5 cm. Lobe Width: Average range 4.0 to 6.0 cm. Quantity: Double flower, petals are very numerous (>100). Texture: Silky, resistant. Lobe Apex: Rounded. Lobe shape: Obovate. Margin: Entire, finely crenate. Aspect: Obovate, fan-shape, concave. Color when opening: Upper surface: RHS Pink 49D. Lower surface: RHS Pink 49D. Color Fully opened: Upper surface: RHS Pink 49D. Lower surface: RHS Pink 49D.

*Calyx/sepals.*—Quantity per flower: 5. Shape: Concave, moderately incurved. Length: Average range 2.5 to 3.0 cm. Width: Average range 1.5 to 2.0 cm. Apex: Acute. Base: Flat. Margin: Entire. Texture: Lower surface: Glabrous. Upper surface: Tomentose. Color: Upper Surface: RHS Yellow-Green 146D. Lower Surface: RHS Yellow-Green 144A, with Green 138A along venations.

*Peduncle.*—None.

*Pedicel.*—Length: Average 45 to 50 cm. Diameter: Average 0.7 to 0.9 cm. Color: RHS Yellow-Green 144A. Orientation: Upright. Pubescence: Slightly tomentose.

*Fragrance.*—None.

Reproductive organs:

*Androecium.*—Stamens: Present, with a short white filament. Anther shape: Longer than wide. Anther length: 0.1 to 0.3 cm. Anther color: RHS Yellow 7A, Red-Purple N79D at the center.

*Gynoecium.*—The pistils are numerous, short, locked together at the center of the corolla, dome-shaped apocarpous gynoecium. Pistil color: RHS Red-Purple N79D. Nectar glands: Absent.

Other characteristics:

*Disease resistance.*—Neither resistance nor susceptibility to normal diseases and pests of *Ranunculus* observed.

*Drought tolerance and cold tolerance.*—No differences have been noted in comparison to the common tolerance characteristics to other *Ranunculus* cultivars.

*Fruit/seed production.*—Not observed.

What is claimed is:

1. A new and distinct cultivar of *Ranunculus* plant named 'ABOTSO' as herein illustrated and described.

* * * * *